(12) United States Patent
Cabiri

(10) Patent No.: US 9,492,610 B2
(45) Date of Patent: *Nov. 15, 2016

(54) NEEDLE ASSEMBLY FOR DRUG PUMP

(71) Applicant: MEDIMOP Medical Projects Ltd., Ra'anana (IL)

(72) Inventor: Oz Cabiri, Macabim-Ruet (IL)

(73) Assignee: MEDIMOP Projects Ltd., Ra'anana (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/931,439

(22) Filed: Nov. 3, 2015

(65) Prior Publication Data

US 2016/0051756 A1 Feb. 25, 2016

Related U.S. Application Data

(63) Continuation of application No. 14/553,399, filed on Nov. 25, 2014, which is a continuation of application (Continued)

(30) Foreign Application Priority Data

Oct. 11, 2010 (IL) .......................................... 208634

(51) Int. Cl.
*A61M 5/142* (2006.01)
*A61M 5/158* (2006.01)
(Continued)

(52) U.S. Cl.
CPC .......... *A61M 5/14248* (2013.01); *A61M 5/158* (2013.01); *A61M 5/1626* (2013.01); *A61M 5/322* (2013.01); *A61M 5/3204* (2013.01); *A61M 5/3287* (2013.01); *A61M 2005/1585* (2013.01)

(58) Field of Classification Search
CPC ............. A61M 5/158; A61M 5/1626; A61M 5/3243; A61M 25/0631; A61M 2005/1585; A61M 2005/14252; A61M 2005/325

USPC ............................ 604/162, 164.08, 263, 302
See application file for complete search history.

(56) References Cited

U.S. PATENT DOCUMENTS 1,795,630 A  3/1931  Wilson
2,860,635 A  11/1958  Wilburn
(Continued)

FOREIGN PATENT DOCUMENTS

CN  1747683 A  3/2006
CN  1863566 A  11/2006
(Continued)

OTHER PUBLICATIONS

Office Action issued Feb. 19, 2016 in U.S. Appl. No. 14/553,399 by Cabiri.
(Continued)

*Primary Examiner* — Gerald Landry, II
(74) *Attorney, Agent, or Firm* — Panitch Schwarze Belisario & Nadel

(57) ABSTRACT

An apparatus (110) includes an activation mechanism (20) and a safety latch (122). The activation mechanism is operative to deploy a needle (116) to protrude out of a housing (112), the needle (116) having a longitudinal axis. The safety latch (122) is movably mounted on the housing (112) and formed with a needle opening (129) to allow the needle (116) to pass therethrough. The safety latch (122) has a first position wherein the needle (116) is aligned to pass through the needle opening (129) and a second position wherein the safety latch (122) is moved with respect to the housing (112) such that the needle (116) is blocked from movement in a direction parallel to the longitudinal axis thereof by a portion of the safety latch (122) distanced from the needle opening (129).

5 Claims, 12 Drawing Sheets

Related U.S. Application Data

No. 14/258,661, filed on Apr. 22, 2014, now Pat. No. 9,149,575, which is a continuation of application No. 13/521,167, filed as application No. PCT/US2011/021604 on Jan. 19, 2011, now Pat. No. 8,915,882, which is a continuation-in-part of application No. 12/689,249, filed on Jan. 19, 2010, now Pat. No. 8,348,898.

(51) Int. Cl.
   *A61M 5/32* (2006.01)
   *A61M 5/162* (2006.01)

(56) References Cited

U.S. PATENT DOCUMENTS

| | | |
|---|---|---|
| 3,203,269 A | 8/1965 | Perrine |
| 3,212,685 A | 10/1965 | Swan et al. |
| 3,794,028 A | 2/1974 | Mueller et al. |
| 3,994,295 A | 11/1976 | Wulff |
| 4,195,636 A | 4/1980 | Behnke |
| 4,218,724 A | 8/1980 | Kaufman |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,685,903 A | 8/1987 | Cable et al. |
| 4,698,055 A | 10/1987 | Sealfon |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,919,596 A * | 4/1990 | Slate ............... G05D 7/0688 417/18 |
| 4,929,241 A | 5/1990 | Kulli |
| 4,950,246 A | 8/1990 | Muller |
| D322,671 S | 12/1991 | Szwarc |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A | 1/1995 | Michel |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,686 A | 10/1996 | Sauer et al. |
| 5,593,390 A | 1/1997 | Castellano et al. |
| 5,616,132 A | 4/1997 | Newman |
| 5,643,218 A | 7/1997 | Lynn et al. |
| 5,645,955 A | 7/1997 | Maglica |
| 5,647,853 A | 7/1997 | Feldmann et al. |
| 5,662,678 A | 9/1997 | Macklin |
| 5,672,160 A | 9/1997 | Osterlind et al. |
| 5,690,618 A | 11/1997 | Smith et al. |
| D393,314 S | 4/1998 | Meisner et al. |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,814,020 A | 9/1998 | Gross |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,931,814 A | 8/1999 | Alex et al. |
| 5,941,850 A | 8/1999 | Shah et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,632,201 B1 | 10/2003 | Mathias et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 6,972,002 B2 * | 12/2005 | Thorne ............ A61M 25/0631 604/164.08 |
| 6,997,727 B1 | 2/2006 | Legrady et al. |
| 7,001,360 B2 | 2/2006 | Veasey et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,097,637 B2 | 8/2006 | Triplett et al. |
| 7,128,727 B2 | 10/2006 | Flaherty et al. |

(56) References Cited

U.S. PATENT DOCUMENTS

| | | |
|---|---|---|
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |

(56) References Cited

U.S. PATENT DOCUMENTS

| | | |
|---|---|---|
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,920,374 B2 | 12/2014 | Bokelman et al. |
| 9,061,104 B2 | 6/2015 | Daniel |
| 9,061,110 B2 | 6/2015 | Avery et al. |
| 9,072,827 B2 | 7/2015 | Cabiri |
| 9,089,475 B2 | 7/2015 | Fangrow |
| 9,089,641 B2 | 7/2015 | Kavazov |
| 2001/0025168 A1 | 9/2001 | Gross et al. |
| 2001/0041869 A1 | 11/2001 | Causey et al. |
| 2002/0010423 A1 | 1/2002 | Gross et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0161332 A1 | 10/2002 | Ramey |
| 2002/0169215 A1 | 11/2002 | Meng |
| 2003/0009133 A1 | 1/2003 | Ramey |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2003/0181868 A1 | 9/2003 | Swenson |
| 2004/0010207 A1 | 1/2004 | Flaherty et al. |
| 2004/0092873 A1 | 5/2004 | Moberg |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0186424 A1 | 9/2004 | Hjertman |
| 2004/0260233 A1 | 12/2004 | Garibotto et al. |
| 2005/0033234 A1 | 2/2005 | Sadowski et al. |
| 2005/0049553 A1 | 3/2005 | Triplett et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | DiIanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173410 A1 | 8/2006 | Moberg et al. |
| 2006/0173439 A1 | 8/2006 | Thorne et al. |
| 2006/0195029 A1 | 8/2006 | Shults et al. |
| 2006/0211982 A1 | 9/2006 | Prestrelski et al. |
| 2006/0229569 A1 | 10/2006 | Lavi et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0106218 A1 | 5/2007 | Yodfat et al. |
| 2007/0118405 A1 | 5/2007 | Campbell et al. |
| 2007/0129688 A1 | 6/2007 | Scheurer et al. |
| 2007/0167912 A1* | 7/2007 | Causey ............. A61M 5/14244 604/131 |
| 2007/0185449 A1 | 8/2007 | Mernoe |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0195049 A1* | 8/2008 | Thalmann ............. A61M 5/158 604/164.01 |
| 2008/0208138 A1 | 8/2008 | Lim et al. |
| 2008/0215006 A1 | 9/2008 | Thorkild |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0275407 A1* | 11/2008 | Scheurer ............... A61M 5/158 604/272 |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0041805 A1 | 2/2009 | Walker |
| 2009/0043253 A1 | 2/2009 | Podaima |
| 2009/0048347 A1 | 2/2009 | Cohen et al. |
| 2009/0054750 A1 | 2/2009 | Jennewine |
| 2009/0054852 A1 | 2/2009 | Takano et al. |
| 2009/0062767 A1* | 3/2009 | Van Antwerp ....... A61B 5/0031 604/504 |
| 2009/0069784 A1 | 3/2009 | Estes et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0139724 A1* | 6/2009 | Gray ...................... E21B 23/04 166/345 |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |

(56) References Cited

U.S. PATENT DOCUMENTS

| | | |
|---|---|---|
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0152658 A1 | 6/2010 | Hanson et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0274202 A1* | 10/2010 | Hyde .............. A61B 5/1405 604/272 |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0125056 A1 | 5/2011 | Merchant |
| 2011/0144584 A1 | 6/2011 | Wozencroft |
| 2011/0160654 A1 | 6/2011 | Hanson et al. |
| 2011/0160655 A1* | 6/2011 | Hanson ............ A61M 5/1413 604/67 |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178472 A1 | 7/2011 | Cabiri |
| 2011/0201998 A1 | 8/2011 | Pongpairochana et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041414 A1 | 2/2012 | Estes et al. |
| 2012/0059332 A1 | 3/2012 | Woehr et al. |
| 2012/0071819 A1* | 3/2012 | Bruggemann .... A61M 5/14546 604/67 |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0296799 A1 | 11/2013 | Degtiar et al. |
| 2013/0304021 A1 | 11/2013 | Cabiri et al. |
| 2013/0323699 A1 | 12/2013 | Edwards et al. |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

FOREIGN PATENT DOCUMENTS

| | | |
|---|---|---|
| CN | 101090749 A | 12/2007 |
| CN | 201941304 U | 8/2011 |
| CN | 102186733 A | 9/2011 |
| DE | 1064693 B | 9/1959 |
| EP | 0017412 A1 | 10/1980 |
| EP | 0222656 A1 | 5/1987 |
| EP | 0401179 A1 | 12/1990 |
| EP | 1530979 A1 | 5/2005 |
| EP | 1666080 A1 | 6/2006 |
| EP | 2060606 A1 | 5/2009 |
| EP | 2498589 A1 | 9/2012 |
| JP | H07-194701 A | 8/1995 |
| JP | H09-505758 A | 6/1997 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-527138 A | 9/2003 |
| JP | 2003-534061 A | 11/2003 |
| JP | 2004-501721 A | 1/2004 |
| JP | 2004-512100 A | 4/2004 |
| JP | 2005-523127 A | 8/2005 |
| JP | 2005-270629 A | 10/2005 |
| JP | 2007-509661 A | 4/2007 |
| JP | 2008-534131 A | 8/2008 |
| JP | 2008-220961 A | 9/2008 |
| JP | 2009-502273 A | 1/2009 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0234315 A1 | 5/2002 |

(56) References Cited

FOREIGN PATENT DOCUMENTS

| | | |
|---|---|---|
| WO | 02072182 A1 | 9/2002 |
| WO | 03090833 A1 | 11/2003 |
| WO | 2004032990 A2 | 4/2004 |
| WO | 2004105841 A1 | 12/2004 |
| WO | 2005018703 A2 | 3/2005 |
| WO | 2005037350 A2 | 4/2005 |
| WO | 2006037434 A1 | 4/2006 |
| WO | 2006069380 A1 | 6/2006 |
| WO | 2006102676 A1 | 9/2006 |
| WO | 2006104806 A2 | 10/2006 |
| WO | 2007051563 A1 | 5/2007 |
| WO | 2007056504 A1 | 5/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009044401 | 4/2009 |
| WO | 2009046989 A2 | 4/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2011075105 A1 | 6/2011 |
| WO | 2011090955 A1 | 7/2011 |
| WO | 2011090956 A2 | 7/2011 |
| WO | 2011156373 A1 | 12/2011 |
| WO | 2012032411 A2 | 3/2012 |
| WO | 2012040528 A1 | 3/2012 |
| WO | 2012160157 A1 | 11/2012 |
| WO | 2014179774 A1 | 11/2014 |

OTHER PUBLICATIONS

Notice of Allowance issued Apr. 25, 2016 in U.S. Appl. No. 14/553,399 by Cabiri.
Daikyo Crystal Zenith® polymer, Manufactured by Daikyo Seiko, Ltd. (Jun. 25, 2008).
Copaxone®, Manufactured by Teva Pharmaceutical Industries Ltd. (2009).
Int'l Search Report issued Apr. 26, 2010 in Int'l Application No. PCT/US2009/069552.
International Preliminary Report on Patentability issued on Jul. 5, 2011 in International Application No. PCT/US2009/069552; Written Opinion.
Office Action issued Sep. 6, 2011 in U.S. Appl. No. 12/345,818.
Office Action issued Feb. 21, 2012 in U.S. Appl. No. 12/689,249.
Int'l Search Report issued Jun. 17, 2011 in Int'l Application No. PCT/US2011/021604.
U.S. Appl. No. 13/521,167 by Cabiri, filed Jul. 9, 2012.
U.S. Appl. No. 13/429,840 by Cabiri, filed Mar. 26, 2012.
Int'l Preliminary Report on Patentability issued Aug. 2, 2012 in Int'l Application No. PCT/US2011/021604.
Int'l Preliminary Report on Patentability issued Feb. 7, 2013 in Int'l Application No. PCT/US2011/021604.
Int'l Search Report and Written Opinion issued Aug. 5, 2013 in Int'l Application No. PCT/US2013/033118.
Office Action issued Oct. 9, 2013 in IL Application No. 208634.
Office Action issued Nov. 4, 2013 in EP Application No. 11 709 234.6.
Office Action issued Dec. 10, 2013 in CN Application No. 201180006567.4.
Office Action issued Jan. 8, 2014 in U.S. Appl. No. 13/521,167 by Cabiri.
Extended European Search Report issued Mar. 27, 2014 in EP Application No. 14154717.4.
U.S. Appl. No. 14/258,661 by Cabiri, filed Apr. 22, 2014.
Office Action issued Sep. 2, 2014 in JP Application No. 2012-550068.
Office Action issued Aug. 26, 2014 in CN Application No. 201180006567.4.
Int'l Preliminary Report on Patentability issued Oct. 9, 2014 in Int'l Application No. PCT/US2013/033118.
U.S. Appl. No. 14/553,399 by Cabiri, filed Nov. 25, 2014.
Office Action issued Nov. 21, 2014 in U.S. Appl. No. 13/429,840 by Cabiri.
Office Action issued Feb. 24, 2015 in U.S. Appl. No. 14/258,661 by Cabiri.
Office Action issued Mar. 10, 2015 in CN Application No. 201180006567.4.
Office Action issued Mar. 31, 2015 in JP Application No. 2012-550068.
U.S. Appl. No. 14/715,791 by Cabiri, filed May 19, 2015.
Office Action issued Aug. 13, 2015 in U.S. Appl. No. 14/553,399 by Cabiri.
Office Action issued Nov. 6, 2015 in U.S. Appl. No. 14/715,791 by Cabiri.
Office Action issued Dec. 17, 2015 in CN Application No. 201380017192.0.
Office Action issued Jul. 1, 2016 in U.S. Appl. No. 15/132,740 by Cabiri.

* cited by examiner

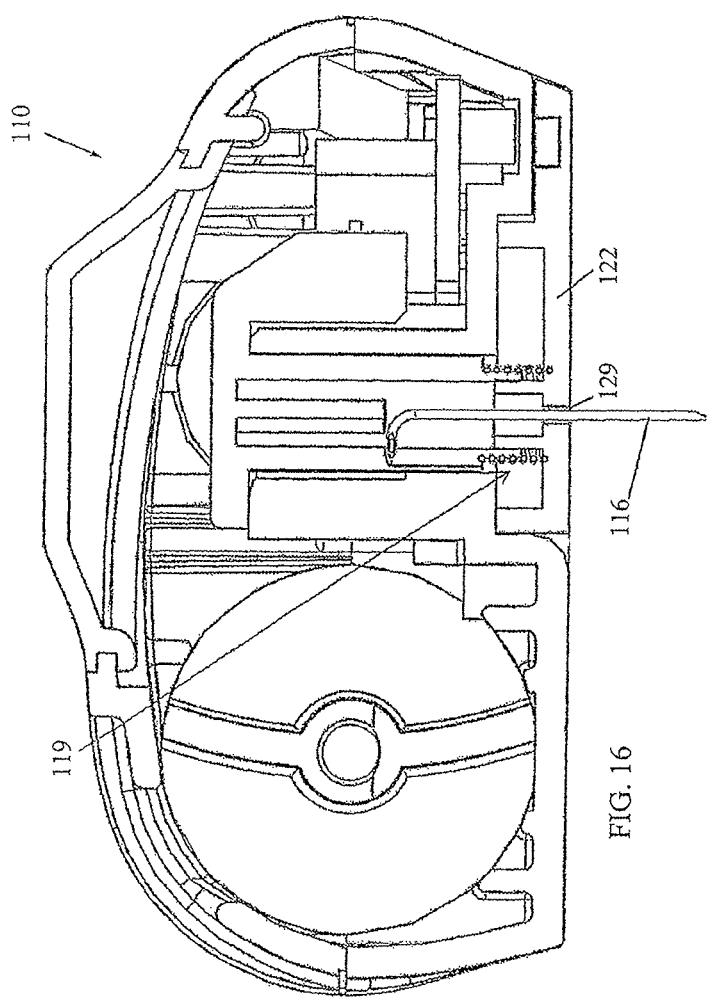

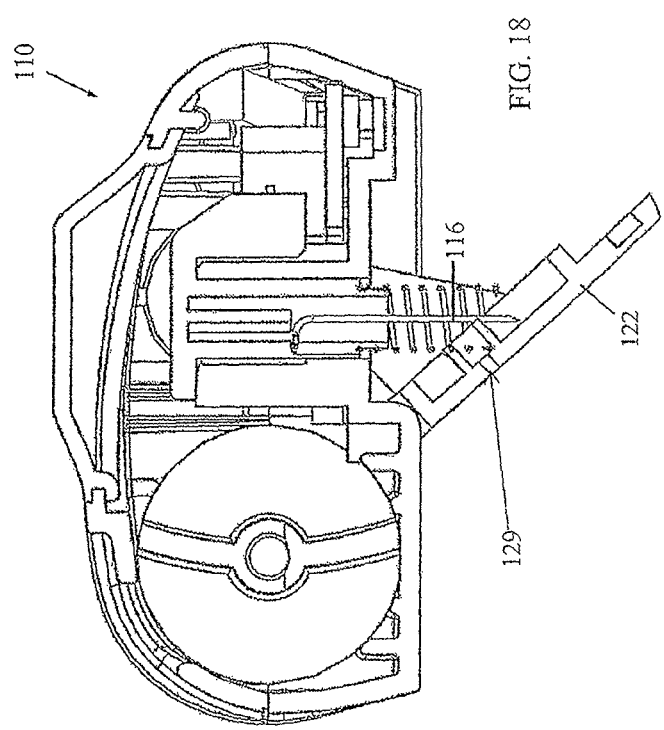

NEEDLE ASSEMBLY FOR DRUG PUMP

CROSS-REFERENCE TO RELATED APPLICATIONS

This application is a continuation of U.S. patent application Ser. No. 14/553,399, filed Nov. 25, 2014, which is a continuation of U.S. patent application Ser. No. 14/258,661, filed Apr. 22, 2014, now U.S. Pat. No. 9,149,575, which is a continuation of U.S. patent application Ser. No. 13/521,167, filed Jul. 9, 2012, now U.S. Pat. No. 8,915,882, which is a section 371 of International Application No. PCT/US2011/021604, filed Jan. 19, 2011, which was published in the English language on Jul. 28, 2011 under International Publication No. WO 2011/090955, which is a continuation-in-part of U.S. patent application Ser. No. 12/689,249, filed Jan. 19, 2010, now U.S. Pat. No. 8,348,898, the disclosures of which are incorporated herein by reference.

BACKGROUND OF THE INVENTION

The present invention generally relates to external drug pumps, and particularly to a needle assembly for a drug pump, particularly suitable for elderly, invalid or physically challenged persons.

External drug pumps are typically used to deliver to patients substances which contain large molecules which cannot be digested when administered orally, such as insulin. Typically, the pump is adhered to the abdomen of the patient and delivers the substance to the patient via a cannula or needle that is inserted into the patient's skin.

U.S. patent application Ser. No. 12/345,818 filed Dec. 30, 2008, and PCT Patent Application PCT/US09/69552, filed Dec. 27, 2009, to the same inventor, describe a needle assembly for administering a drug from a vial. (The terms "drug" and "substance" are used interchangeably throughout the specification and claims, and encompass any material administered to a subject. The term "cartridge" throughout the specification and claims encompasses any container for a drug, such as but not limited to, a cartridge, vial, syringe, bottle, ampoule and many more, and is not limited to any size or shape.) The needle assembly includes a needle held in a needle holder, and an activation mechanism for activating delivery of the substance through the needle, such as a push button that initiates the delivery of the substance. The activation mechanism includes a safety latch that prevents the needle from pricking a person accidentally and prevents inadvertent administration of the drug. The safety latch initially impedes movement of the needle holder. When the safety latch is placed on the subject, the safety latch moves to a position that permits moving the needle holder to cause the needle to protrude outwards of the housing to pierce the subject to allow administration of the substance to the subject.

A problem of this prior art needle assembly is that elderly, invalid or physically challenged persons may find it difficult to push the push button to activate delivery of the substance.

BRIEF SUMMARY OF THE INVENTION

In accordance with an aspect of the invention, there is provided an apparatus comprising an activation mechanism and a safety latch. The activation mechanism is operative to deploy a needle to protrude out of a housing, said needle having a longitudinal axis. The safety latch is movably mounted on said housing and formed with a needle opening to allow said needle to pass therethrough. The safety latch has a first position wherein said needle is aligned to pass through said needle opening and a second position wherein said safety latch is moved with respect to said housing such that said needle is blocked from movement in a direction parallel to the longitudinal axis thereof by a portion of said safety latch distanced from said needle opening.

BRIEF DESCRIPTION OF THE DRAWINGS

The present invention will be understood and appreciated more fully from the following detailed description taken in conjunction with the drawings in which:

FIG. 16 is a simplified illustration of the inside of the apparatus in the position of FIG. 15;

FIG. 18 is a simplified illustration of the inside of the apparatus in the position of FIGS. 17A-17B.

DETAILED DESCRIPTION OF THE INVENTION

Figure 1:
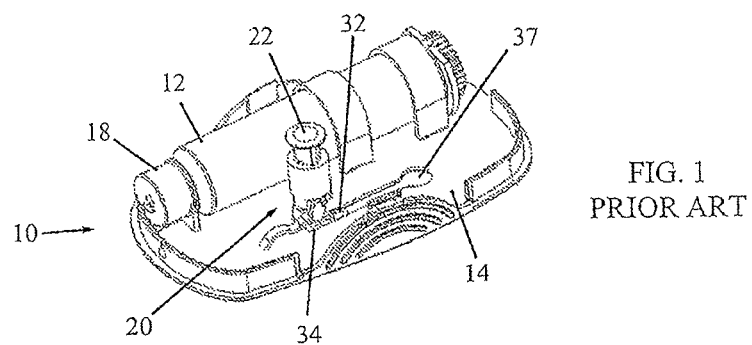
FIG. 1 is a simplified illustration of apparatus for administering a substance to a subject, from the prior art (U.S. patent application Ser. No. 12/345,818 or PCT Patent Application PCT/US09/69552)

Reference is now made to FIG. 1, which illustrates apparatus 10 for administering a substance, for example, insulin, to a subject, from the prior art (U.S. patent application Ser. No. 12/345,818 or PCT Patent Application PCT/US09/69552.

A cartridge 12 (also referred to as a vial, the terms being used interchangeably) is mounted on a housing base 14. For some applications, a cartridge piercing mechanism 18 is movably (e.g., rotatably) coupled to housing base 14 and pierces the distal end of cartridge 12. The substance to be administered flows from cartridge 12 to an activation mechanism 20 via a tube (not shown). The activation mechanism 20 has a control button 22 and is typically coupled to the housing base 14. The activation mechanism 20 is configured to insert a cannula and/or a needle through the subject's skin and to deliver the substance via the cannula and/or the needle. The embodiments of the invention are described with reference to a needle alone, but apply as well to a needle disposed in a cannula or any other delivery device. The term "needle" is used throughout the specification and claims to encompass all such delivery devices.

Apparatus 10 typically includes a motor, a battery and a control unit (all not shown). After the needle has penetrated the skin of the patient, the control unit controls operation of the motor to administer a controlled amount of the substance to the patient at a controlled rate of delivery. Of course, the needle assembly of the present invention can be used in other applications and does not have to be used with a controlled motorized delivery system.

Figure 2:
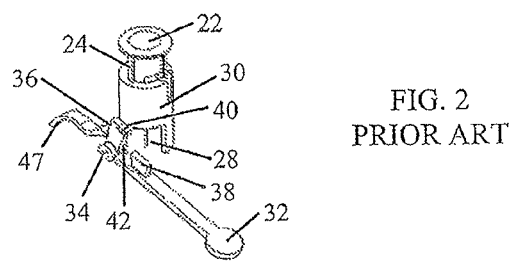
FIG. 2 is a simplified illustration of a safety latch of the prior art apparatus in the down position, this being the nominal (starting) position as long as the apparatus has not yet been placed upon the user's body, and a needle holder cannot be pushed down.
Figure 3:
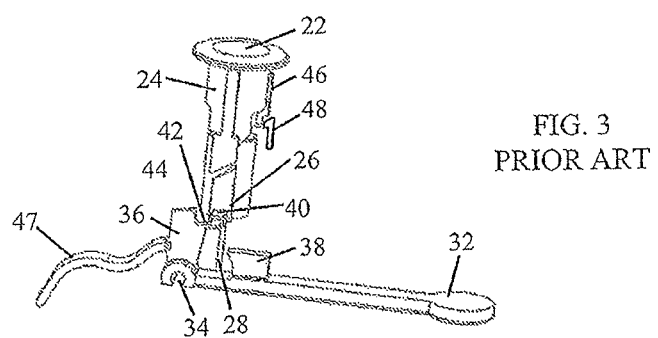
FIG. 3 is a simplified illustration of the prior art safety latch in the up position, which is the position when the apparatus has been placed upon the user's skin.

Reference is now made to FIGS. 2 and 3, which illustrate a safety latch of the prior art. Control button 22 has a shaft 24 which is arranged to move (vertically downwards in the sense of the drawings) against a needle holder 26 (FIG. 3) which holds a needle 28. The shaft 24 and the needle holder 26 are both confined to move in a (e.g., tubular) housing 30, but there is a difference in their movements. Shaft 24 is confined to translate downwards in housing 30 with no rotation. In contrast, needle holder 26 can not only translate but can also rotate in housing 30, as will be explained more in detail below.

The movement of needle holder 26 is selectively impeded by a safety latch 32, which is pivotally mounted on housing base 14 about a pivot 34. Safety latch 32 is arranged to selectively pivot in and out of a complimentary shaped groove 37 (FIG. 1) formed in housing base 14. Safety latch 32 includes a first arrestor 36 at a distal end thereof and a second arrestor 38 proximal to and spaced from the first arrestor 36. The arrestors may be shaped as lugs or other projections or any other structure suitable for arresting motion of needle holder 26 as will be explained below.

FIG. 2 shows safety latch 32 in the down position, which is its nominal (starting) position as long as apparatus 10 has not yet been placed upon the user's body. In this position, first arrestor 36 abuts against an ear 40 that projects from a bottom portion of needle holder 26. It is noted that pushing ear 40 down against a surface 42 of first arrestor 36 will not cause downward movement of needle holder 26 because this will simply pivot first arrestor 36 about the pivot 34 causing another surface 44 of first arrestor 36 to abut against the bottom surface of housing 30. Thus, when safety latch 32 is in the down position, needle holder cannot be pushed down (in the sense of the drawing of course).

FIG. 3 shows safety latch 32 in the up position (that is, it has pivoted upwards about pivot 34), which is the position when apparatus 10 has been placed upon the user's skin. First arrestor 36 has been moved out of the way of ear 40 of needle holder 26, so that control button 22 can now be pressed down to move needle holder 26 downward, thereby piercing the patient's skin. Needle 28 remains inserted in the patient for the duration of the drug administration. Pressing control button 22 down causes shaft 24 to become locked in the down position in housing 30, such as by means of one or more splines (not shown here), which radially project outwards from shaft 24, sliding past one or more chamfered resilient tongues (not shown here) mounted in housing 30. After the splines slide past tongues, the splines become locked in place by the action of the tongues resiliently snapping back in place over them.

Figure 4:
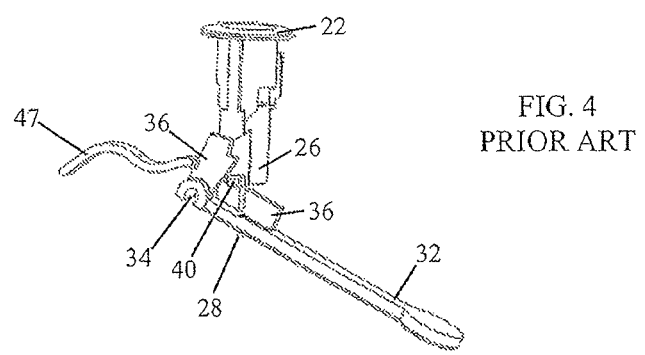
FIG. 4 is a simplified illustration of lifting the prior art apparatus off the patient's body after finishing the drug administration, which causes the safety latch to move back to the down position.
Figure 5:
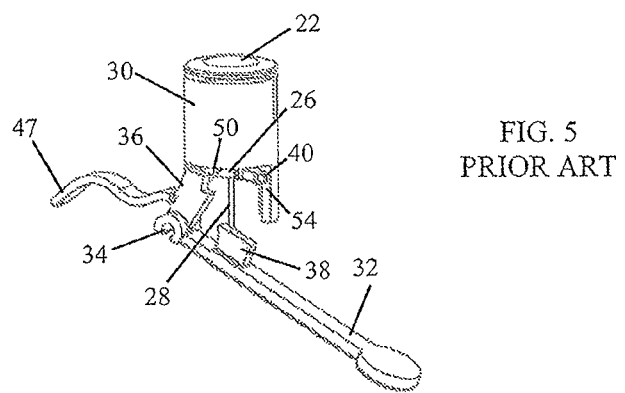
FIG. 5 is a simplified illustration of the prior art needle holder moving back up and getting stopped in the up position with the needle retracted back into the housing of the apparatus.

After finishing the drug administration, apparatus 10 is lifted off the patient's body. This causes safety latch 32 to move back to the down position as shown in FIG. 4, thereby moving second arrestor 38 away from ear 40. A biasing device 47, such as a leaf spring biased between first arrestor 36 and housing base 14, may be employed to impart a returning force on safety latch 32 to move it back to the down position. A slanted tongue 50 applies a downward force on ramp 52, thereby permitting needle holder 26 to rotate counterclockwise until slanted tongue 50 slides off ramp 52. At this point, needle holder 26 jumps back up and ear 40 gets caught on a shoulder 54 formed on housing 30 as shown in FIG. 5. In this position, needle bolder 26 cannot move back down because of ear 40 being arrested against shoulder 54. Accordingly, needle 28 is trapped back inside apparatus 10 in a safe position, and apparatus 10 may be safely discarded.

Figure 6:
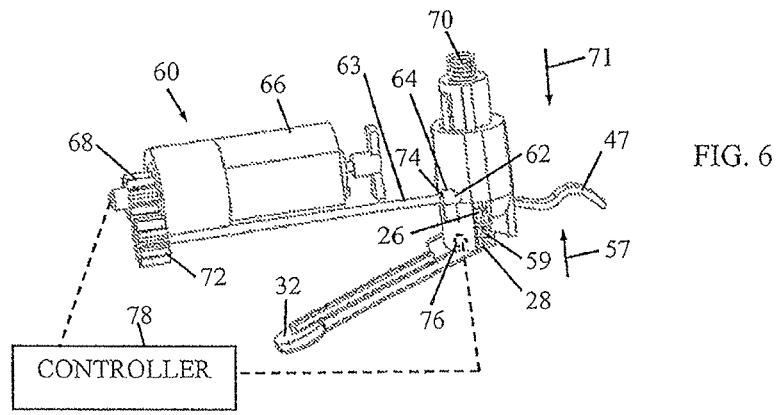
FIG. 6 is a simplified illustration of biasing device release apparatus used in administering a substance to a subject, constructed and operative in accordance with an embodiment of the present invention.

Reference is now made to FIG. 6, which illustrates biasing device release apparatus 60 for administering a substance to a subject, constructed and operative in accordance with an embodiment of the present invention. Elements of the present invention which are identical or equivalent to elements described above for the prior art are designated with the same reference numerals.

As previously described, in the prior art apparatus, after drug administration, needle bolder 26 retracts back into housing 30 by the action of counterclockwise rotation and ear 40 getting caught on shoulder 54 formed on housing 30. In the present invention, this same arrangement can be used. Alternatively or additionally, a biasing device 59, such as a coil spring, can be used to retract needle holder 26 back into housing 30 after drug administration. Biasing device 59 is arranged to apply an urging force on needle 28 in the direction of arrow 57 (upwards in the sense of the drawings).

With biasing device release apparatus 60, the user does not have to apply a force for the mechanical operation of the device. Rather either there is no control button to push down, or alternatively the control button can be touch sensitive or be operated on slight pressure, and a biasing device 70, such as a coil spring, is released to push down needle 28, as described below. Biasing device 70 is stronger than biasing device 59. Biasing device 70 is arranged to apply an urging force on needle 28 in the direction of arrow 71 (downwards in the sense of the drawings).

Apparatus 60 includes a biasing device arrestor 62, such as a tongue or dog mounted on a shaft 63, and enters housing 30 through an aperture 64. An actuator 66 is provided for moving biasing device arrestor 62. For example, actuator 66 may be, without limitation, a step motor, linear actuator, solenoid and the like. In the non-limiting illustrated embodiment, actuator 66 is a step motor that rotates a drive gear 68 that meshes with a spur gear 72 mounted on shaft 63. Biasing device arrestor 62 may be threadedly mounted on a threaded portion 74 of shaft 63.

Figure 7:
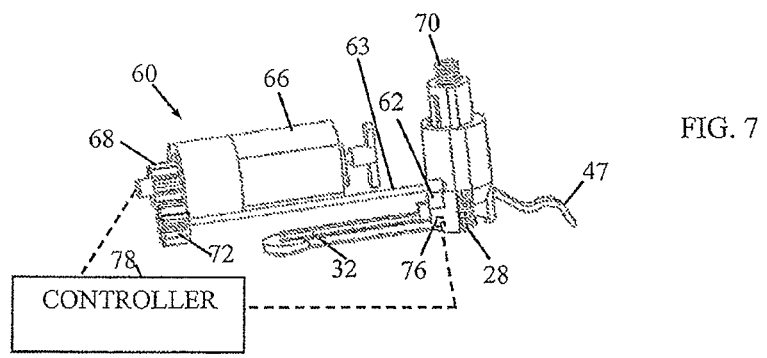
FIG. 7 is a simplified illustration of a safety latch of the biasing device release apparatus of FIG. 6 in the up position, which is the position when the apparatus has been placed upon the user's skin.

A safety latch position sensor 76 is provided for sensing when safety latch 32 moves to the up position of FIG. 7. Safety latch position sensor 76 may be, without limitation, a reed switch or any other kind of switch or sensor suitable for sensing the movement of safety latch 32 to the up position. Safety latch position sensor 76 is in communication with a controller 78, which controls operation of actuator 66. As mentioned above, the prior art apparatus 10 typically includes a motor, a battery and a control unit. Actuator 66 can be this same motor and controller 78 may be this same control unit, or they may be separate units.

FIG. 6 shows safety latch 32 in the down position, which is its nominal (starting) position as long as the drug administering apparatus has not yet been placed upon the user's body, corresponding to FIG. 2 of the prior art. As described above, in this position, needle holder 26 cannot be pushed down (in the sense of the drawing). In the present invention, in this position, biasing device arrestor 62 is inside housing 30 and blocks biasing device 70, preventing it from pushing down on needle 28.

FIG. 7 shows safety latch 32 in the up position (corresponding to FIG. 3 of the prior art), which is the position when the drug administering apparatus has been placed upon the user's skin. Safety latch position sensor 76 senses the movement of safety latch 32 to the up position and signals controller 78 that safety latch 32 is now in the up position. Controller 78 thereupon commences operation of actuator 66. In a preferred embodiment, controller 78 initiates operation of actuator 66 after a predetermined time delay (e.g., 5-15 seconds) to ensure that the drug administration apparatus was indeed placed on purpose on the patient for administering the drug.

Figure 8:
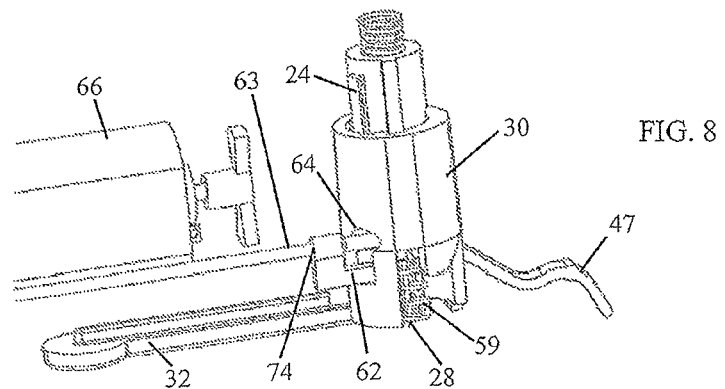
FIG. 8 is a simplified illustration of an actuator moving a biasing device arrestor out of a housing so as not to block a biasing device which can urge a needle of the apparatus to pierce a patient's skin, in accordance with an embodiment of the present invention.

When operated, actuator 66 moves biasing device arrestor 62 out of aperture 64, as shown in FIG. 8. In the non-limiting illustrated embodiment, actuator 66 rotates drive gear 68, which in turn rotates spur gear 72 to rotate shaft 63. Rotation of shaft 63 causes biasing device arrestor 62 to move linearly out of aperture 64 along threaded portion 74. When biasing device arrestor 62 reaches the end of threaded portion 74, it rotates freely on shaft 63 and moves no further.

Figure 9:
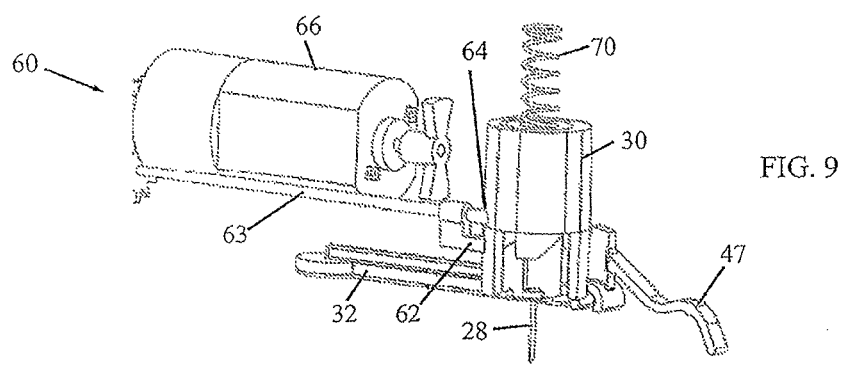
FIG. 9 is a simplified illustration of the biasing device urging the needle to a piercing position, in accordance with an embodiment of the present invention.

As soon as biasing device arrestor 62 has moved out of aperture 64, biasing device 70 is no longer blocked and it now pushes down on needle 28 (overcoming the weaker biasing device 59), as shown in FIG. 9. Needle 28 now piercing the patient's skin and administers the drug. As described for the prior art apparatus, shaft 24 becomes locked in the down position in housing 30.

Figure 10:
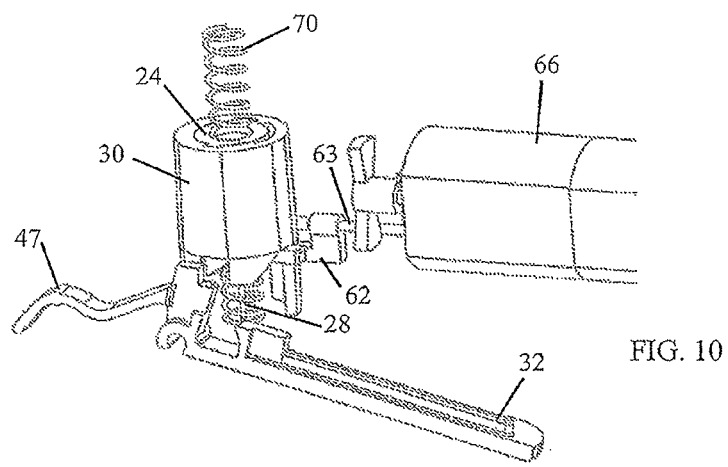
FIG. 10 is a simplified illustration of the biasing device release apparatus lifted off the patient's body after finishing the drug administration, which causes the safety latch to move back to the down position and the needle to be retracted back into the housing.

After finishing the drug administration, the apparatus is lifted off the patient's body. As described for the prior art apparatus, this causes safety latch 32 to move back to the down position as shown in FIG. 10, and needle 28 is trapped back inside the apparatus in a safe position, and the apparatus may be safely discarded.

Figure 11:
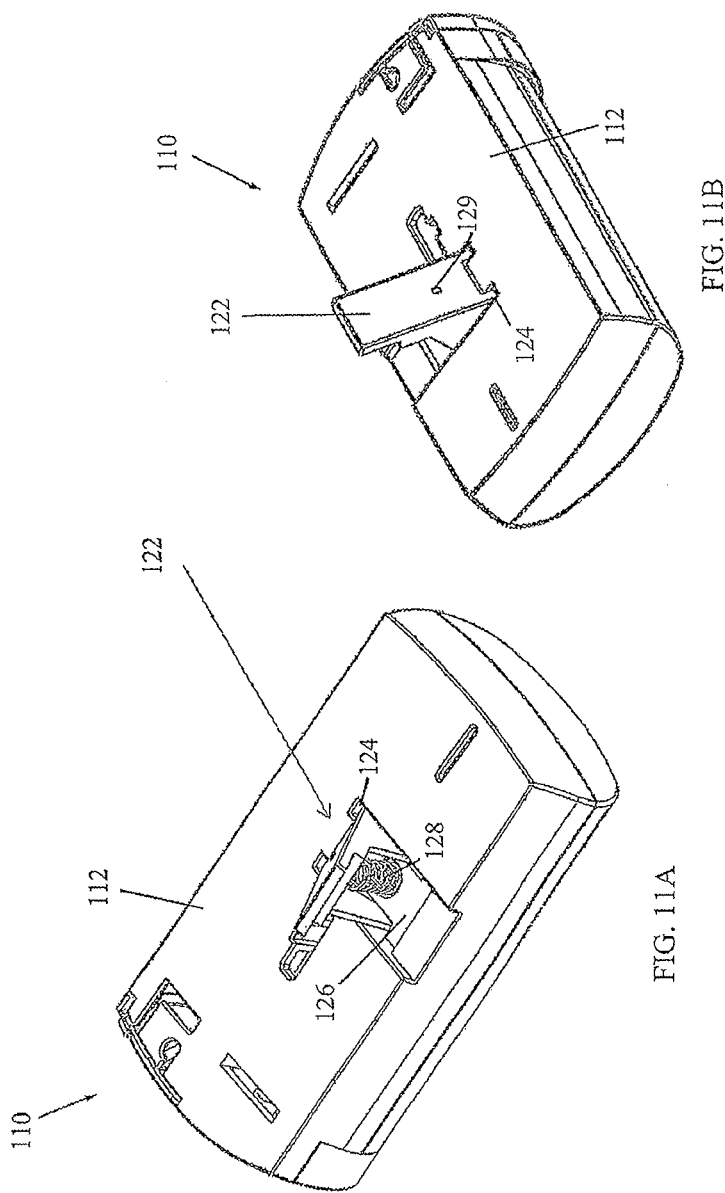
FIGS. 11A and 11B are simplified perspective illustrations of the biasing device release apparatus employed in another apparatus (drug pump) for administering a substance to a subject, constructed and operative in accordance with an embodiment of the present invention.
Figure 12:
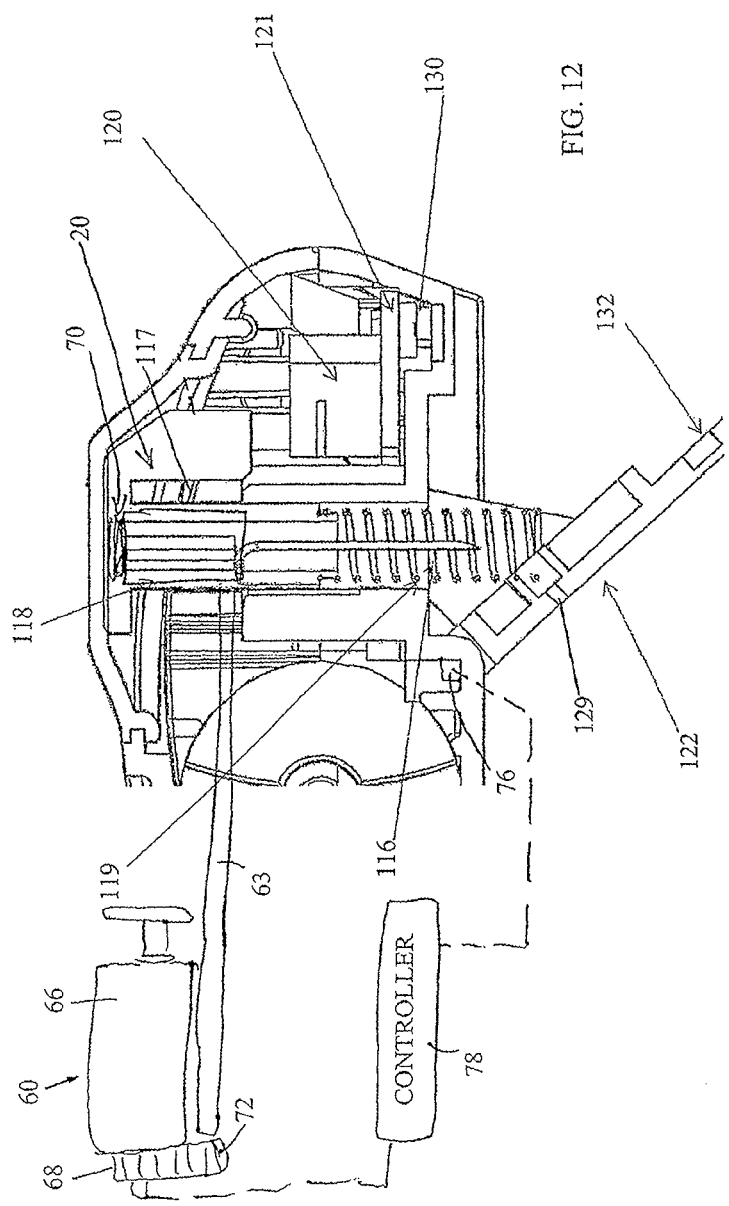
FIG. 12 is a simplified illustration of the inside of the apparatus in the position of FIGS. 11A-11B FIGS. 13A and 13B are simplified perspective illustrations of the apparatus of FIGS. 11A-11B, in a second stage, after application of the apparatus on the patient's body, in accordance with an embodiment of the present invention.

Reference is made to FIGS. 11A-11B and 12, which illustrate the biasing device release apparatus 60 employed in another apparatus 110 (also referred to as drug pump 110) for administering a substance to a subject, constructed and operative in accordance with an embodiment of the present invention. Elements of biasing device release apparatus 60 are designated with the same reference numerals as above.

The activation mechanism 20 is also employed in this embodiment. However, as opposed to the previously described embodiments, in apparatus 110, the needle is not retracted back into the housing after drug administration, but there is a protector that blocks the needle after use for preventing accidental needle pricks, as is described more in detail hereinbelow.

In apparatus 110, the cartridge (not shown) is mounted on a housing base 112 (or simply housing 112), as shown in FIGS. 11A-11B. A hollow needle (not shown) is provided in housing 112 for piercing a septum at a distal end of the cartridge. The substance to be administered flows from the cartridge eventually to a needle 116 held in a needle holder 118 (confined to move in a housing 117), as controlled by biasing device release apparatus 60. As described above, with biasing device release apparatus 60, there is no control button to push down. Instead biasing device 70 is released to push clown needle 116, in the same manner as described above.

The movement of needle holder 118 is selectively impeded by a safety latch 122, which is pivotally mounted on housing base 112 about a pivot 124. Safety latch 122 is arranged to selectively pivot in and out of a complimentary shaped groove 126 formed in housing base 112. Safety latch 122 may be biased by a biasing device 128, such as a coil spring. Safety latch 122 is formed with a needle opening 129 to allow needle 116 to pass therethrough.

In the first stage shown in FIGS. 11A, 11B and 12, before operation, safety latch 122 blocks the path of needle 116 for preventing against inadvertent, premature activation (the blocking mechanism as described, for example, in U.S. patent application Ser. No. 12/345,818 or PCT Patent Application PCT/US09/69552).

A microsensor 120, such as a photo-microsensor, may be provided for sensing the position of the needle for use in conjunction with the control unit to control the various stages of the operation of the pump. In addition to the photo-microsensor 120, another sensor 130 (FIG. 12) may be provided for sensing the position and operation of safety latch 122. For example, sensor 130 may be a magnet sensor 130 that senses if a magnet 132 mounted on the distal end of safety latch 122 is near sensor 130 or not.

Figure 13B:
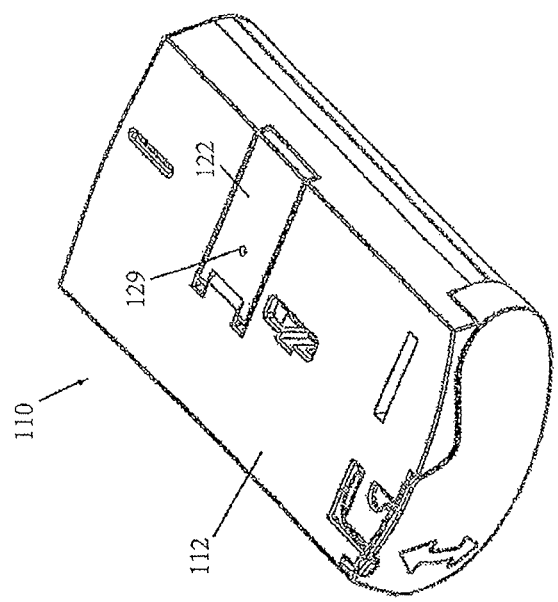
Figure 13A:
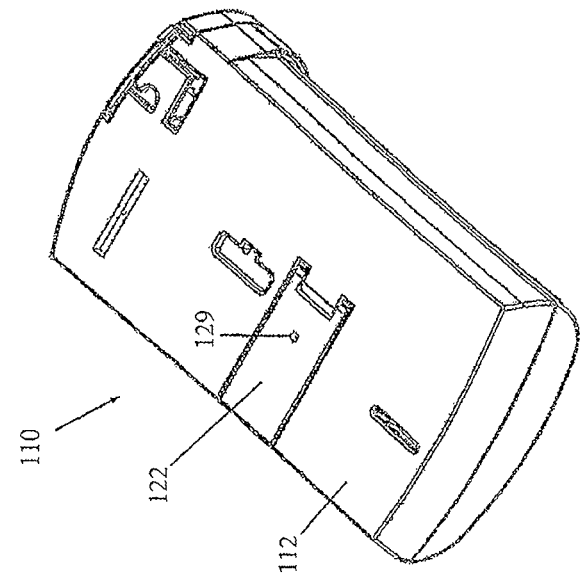
Figure 14:
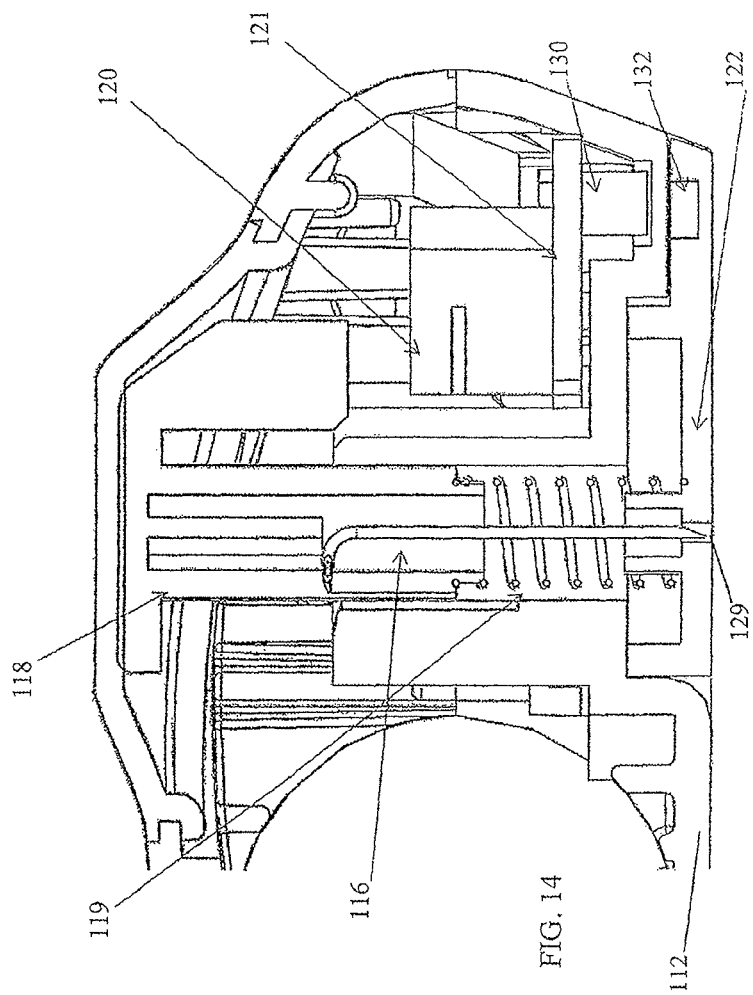
FIG. 14 is a simplified illustration of the inside of the apparatus in the position of FIGS. 13A-13B.

In the second stage shown in FIGS. 13A, 13B and 14, apparatus 110 is placed on the patient's body (not shown), and safety latch 122 has pivoted to be flush with housing base 112. Needle 116 is now aligned to be advanced through needle opening 129 of safety latch 122. An indication may be provided that pump 110 is on the body by magnet sensor 130 sensing the magnet 132 on safety latch 122 (or any other suitable sensing mechanism). (It is noted that biasing device release apparatus 60 is not shown in FIG. 14 for the sake of simplicity.)

Figure 15:
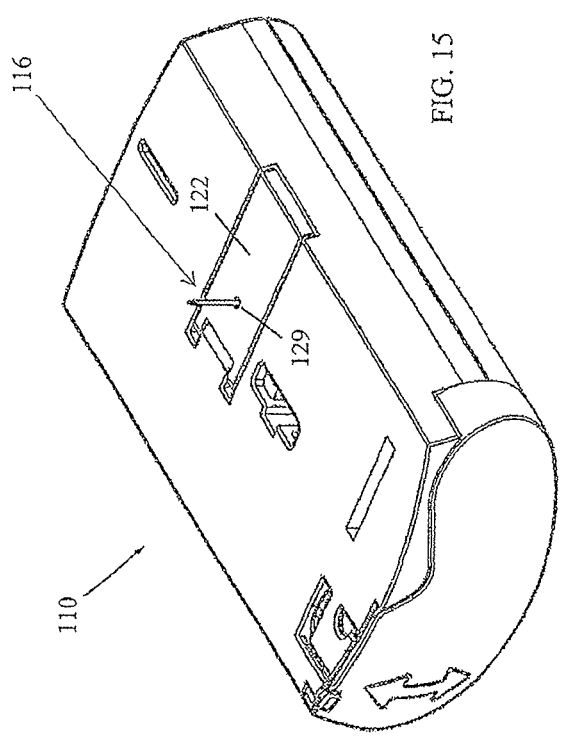
FIG. 15 is a simplified perspective illustration of the apparatus of FIGS. 11A-11B, in a third stage, in which the needle protrudes out of the pump and is inserted in the body, in accordance with an embodiment of the present invention.

As described above, biasing device 70 of biasing device release apparatus 60 is then released to push down needle 116 into the patient's body, in the same manner as described above. Needle 116 advances through needle opening 129 of safety latch 122 to the position shown in FIGS. 15 and 16

(third stage of operation). The sensing mechanism may provide an indication indicating that the needle 116 is inserted. Needle 116 stays locked in the insertion position.

Figure 17B:
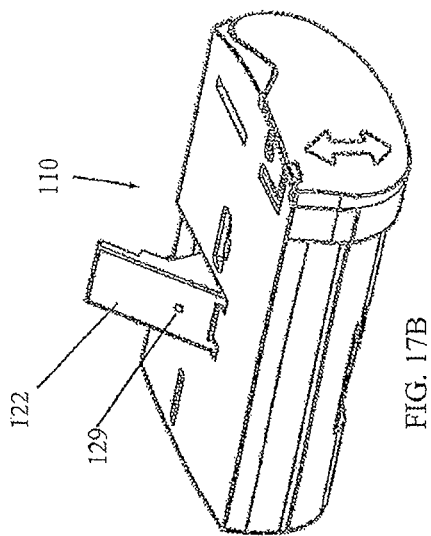
FIGS. 17 A and 17B are simplified perspective illustrations of the apparatus of FIGS. 11A-11B, in a fourth and final stage, after removing the apparatus from the patient's body, in which a protector blocks the needle after use, in accordance with an embodiment of the present invention.
Figure 17A:
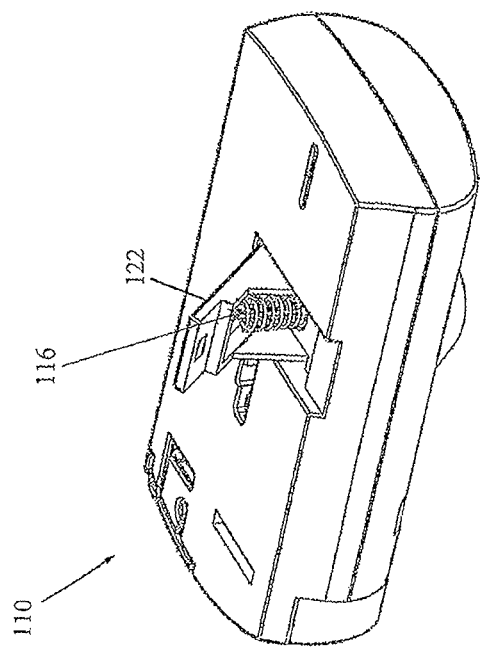

Reference is made to FIGS. 17A, 17B and 18. In the fourth and final stage of operation, after administrating the substance, pump 110 is removed from the patient's body, thereby releasing safety latch 122 to pivot to the down position. However, since needle 116 is already protruding out of the housing and remains locked in the protruded position, needle 116 does not align with needle opening 129 of safety latch 122, as seen best in FIG. 18. Thus, safety latch 122 serves as a protector that blocks the tip of needle 116 after use of pump 110 for preventing accidental needle pricks.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

I claim:

1. A drug delivery device for administering a medicament to a patient comprising:
    a housing having an injection needle therein;
    a needle insertion apparatus for ejecting at least a tip of the injection needle out of the housing;
    a safety latch coupled to the housing and including a needle opening for advancement of at least the tip of the needle therethrough, the latch being movable from a first position prior to use of the drug delivery device to a second position when the drug delivery device is placed on the patient;
    a safety latch position sensor configured to detect at least the second position of the safety latch; and
    an electronic controller electronically coupled with the safety latch position sensor and configured to control operation of the needle insertion apparatus;
    wherein with the housing in contact with the patient, and the safety latch in the second position, the safety latch position sensor electrically signals the electronic controller, which, in turn, initiates operation of the needle insertion apparatus.

2. The drug delivery device of claim 1, wherein the needle insertion apparatus comprises a biasing device, biased to eject the injection needle, a biasing device arrestor blocking movement of the biasing device, and an actuator coupled with the biasing device arrestor and operatively controlled by the electronic controller, wherein the electronic controller initiates the operation of the actuator when the safety latch is in the second position, which withdraws the biasing device arrestor from blocking movement of the biasing device, and, in turn, permitting the biasing device to eject the injection needle.

3. The drug delivery device of claim 2, wherein the electronic controller is configured to initiate the operation of the actuator after a predetermined time delay from receiving the signal from the safety latch position sensor that the safety latch is in the second position.

4. The drug delivery device of claim 3, wherein the predetermined time delay ranges between 5 seconds to 15 seconds.

5. The drug delivery device of claim 1, wherein the safety latch position sensor is a reed switch.

\* \* \* \* \*